US009506879B2

(12) United States Patent
Engelbart et al.

(10) Patent No.: US 9,506,879 B2
(45) Date of Patent: Nov. 29, 2016

(54) METHOD AND SYSTEM FOR NON-DESTRUCTIVELY EVALUATING A HIDDEN WORKPIECE

(71) Applicant: The Boeing Company, Chicago, IL (US)

(72) Inventors: Roger W. Engelbart, St. Louis, MO (US); Taisia Tsukruk Lou, St. Louis, MO (US)

(73) Assignee: The Boeing Company, Chicago, IL (US)

( * ) Notice: Subject to any disclaimer, the term of this patent is extended or adjusted under 35 U.S.C. 154(b) by 9 days.

(21) Appl. No.: 14/505,043

(22) Filed: Oct. 2, 2014

(65) Prior Publication Data

US 2015/0055757 A1   Feb. 26, 2015

Related U.S. Application Data

(63) Continuation-in-part of application No. 13/527,068, filed on Jun. 19, 2012, now Pat. No. 8,873,711.

(51) Int. Cl.
*G01N 23/00*  (2006.01)
*G01N 23/203* (2006.01)
*G01B 15/02*  (2006.01)
*G01N 17/04*  (2006.01)

(52) U.S. Cl.
CPC ............. *G01N 23/203* (2013.01); *G01B 15/02* (2013.01); *G01N 17/043* (2013.01)

(58) Field of Classification Search
CPC ...... G01N 23/203; G01N 9/24; G01N 33/24; G01N 23/02; G01N 23/025; G01N 23/04; G01N 23/08; G01N 23/00; G01N 23/20008; G01N 23/20066; G01N 23/20083; G01N 23/201; G01N 23/223; G01N 23/2252
See application file for complete search history.

(56) References Cited

U.S. PATENT DOCUMENTS 3,611,408 A * 10/1971 Shoemaker ............ G01R 17/00
                                                                 250/252.1
6,000,844 A    12/1999 Cramer et al.
6,459,761 B1 * 10/2002 Grodzins ............... G01N 23/02
                                                                 378/56
7,508,910 B2   3/2009  Safai et al.
7,623,626 B2   11/2009 Safai et al.
(Continued)

OTHER PUBLICATIONS

Runft et al. (WO2011/047945). Apr. 28, 2011.*
(Continued)

*Primary Examiner* — David J Makiya
*Assistant Examiner* — Dani Fox
(74) *Attorney, Agent, or Firm* — Alston & Bird LLP

(57) ABSTRACT

A method and system are provided for non-destructively evaluating a workpiece hidden by an overlying structure. In the context of a method, a workpiece is interrogated with radiation, such as x-ray radiation, that also propagates through the overlying structure. The method further includes collecting data representative of radiation backscattered from the workpiece. Based upon a thickness and material of the overlying structure, the method compares the data that has been collected from the workpiece with reference data representative of radiation backscattered from a standard that includes different respective material loss indicators hidden by an overlying structure of the same thickness and material. Each material loss indicator is a physical representation of a different amount of material loss. As a result of the comparison, the method estimates the material loss of the workpiece.

12 Claims, 6 Drawing Sheets

(56) References Cited

U.S. PATENT DOCUMENTS

| | | |
|---|---|---|
| 7,649,976 B2 | 1/2010 | Georgeson et al. |
| 7,840,363 B2 * | 11/2010 | Stephenson ............ C10G 1/008 |
| | | 702/137 |
| 8,094,781 B1 | 1/2012 | Safai et al. |
| 8,138,471 B1 | 3/2012 | Shedlock et al. |
| 8,761,338 B2 | 6/2014 | Safai |
| 2004/0156737 A1 | 8/2004 | Rakowski |
| 2005/0151841 A1 | 7/2005 | Nelson et al. |
| 2006/0058974 A1 | 3/2006 | Lasiuk et al. |
| 2007/0222436 A1 | 9/2007 | Gao et al. |
| 2008/0307886 A1 | 12/2008 | Marsh et al. |
| 2009/0234590 A1 | 9/2009 | Mcnealy et al. |
| 2012/0240819 A1 | 9/2012 | Hartley et al. |
| 2013/0129041 A1 * | 5/2013 | Runft ..................... A61J 3/074 |
| | | 378/56 |
| 2014/0064459 A1 | 3/2014 | Wahl et al. |

OTHER PUBLICATIONS

Nucsafe—Backscatter Radiography, including two downloaded documents dated 2012; [online] [retrieved Jul. 17, 2012]. Retrieved from the Internet: <URL: http://www.nucsafe/com/cms/Backscatter+Radiography/79.html>. 6 pages.

* cited by examiner

METHOD AND SYSTEM FOR NON-DESTRUCTIVELY EVALUATING A HIDDEN WORKPIECE

CROSS-REFERENCE TO RELATED APPLICATION

This application claims the benefit of and is a continuation-in-part of U.S. patent application Ser. No. 13/527,068, filed Jun. 19, 2012, the contents of which is incorporated by reference herein in its entirety.

TECHNOLOGICAL FIELD

An example embodiment of the present disclosure relates generally to a method and system for non-destructively evaluating a workpiece hidden by an overlying structure.

BACKGROUND

It is oftentimes desirable to inspect a workpiece in order to detect anomalies, such as the effects of corrosion. For example, vehicles, such as aircraft, trains, automobiles and other motor vehicles, and other structures may include a number of structural components that are desirably inspected in order to identify anomalies, such as the effects of corrosion. Although some of the structural components are readily accessible so as to be inspected visually, a number of the structural components, such as the stringers of an aircraft, are positioned in a remote location so as to be hidden from view or to otherwise be of limited access.

For some hidden structures, structural components that are visible and near a hidden structure may be evaluated. An estimate of the condition of the hidden structure may then be derived based upon the condition of the visible structural components near the hidden structure. For example, a beavertail fitting may be attached to a wing skin. A beavertail fitting may be relatively large, such as 17 feet in length for a KC-135 aircraft, and may therefore hide a substantial portion of the wing skin that underlies the beavertail fitting. By evaluating the condition of the wing skin that surrounds and is proximate to the beavertail fitting, such as to identify corrosion, discoloration or pitting, the condition of the portion of the wing skin that underlies and is hidden by the beavertail fitting may be estimated. In an instance in which the wing skin that surrounds and is proximate to the beavertail fitting shows evidence of corrosion, the beavertail fitting may be removed in order to visually inspect the portion of the wing skin underlying the beavertail fitting. The removal and subsequent reattachment of the beavertail fitting following visual inspection of the portion of the wing skin that underlies the beavertail fitting increase the time that the aircraft is out of service and, as a result, may be inefficient in an instance in which the estimate of the condition of the portion of the wing skin that underlies the beavertail fitting is subsequently proven to be incorrect by the visual inspection of the portion of the wing skin that underlies the beavertail fitting.

In order to inspect these hidden structural components as opposed to relying upon an estimate of their condition, a structural assembly may be disassembled and, following inspection, may then be reassembled, thereby resulting in substantial expense and downtime. With respect to an aircraft, for example, the disassembly, inspection and subsequent reassembly may require a number of man hours and lead to significant aircraft downtime at a repair depot. In order to avoid disassembly of a structural assembly, non-destructive inspection techniques have been developed, such as radiography, ultrasonic and eddy current inspection techniques. The type of non-destructive inspection technology that is utilized may be dependent upon the type of anomaly to be detected, the type of material to be inspected, the location at which the inspection will occur and the complexity of the structural assembly in and around the location that will be inspected. For example, the substantial number of fasteners utilized to attach a beavertail fitting to the wing surface may prevent ultrasonic and eddy current inspection techniques from being utilized to inspect the hidden portion of the wing skin that underlies the beavertail fitting, thereby suggesting that a radiographic inspection technique be utilized.

Some remote locations of a structural assembly may be prone to corrosion as a result of the intrusion and retention of moisture. Since the need for corrective action, if any, is dependent upon the severity of the corrosion which may, in turn, be measured by the percent of the total thickness of the structure that has been lost due to corrosive activity, radiography may provide a non-destructive inspection technique to facilitate the inspection of such remote locations without disassembly in order to determine the effects of corrosion. In order to non-destructively inspect a structural component using transmission radiography, an x-ray source may be placed on one side of the structural component and an imaging medium may be placed on the other side of the structural component. As such, while the structural assembly need not necessarily be disassembled during transmission radiography, access is generally required to both sides, that is, the opposite sides of the structural component to be inspected. While access to the opposite sides of a structural component to be inspected is available in some instances, the opposite sides of some structural components may not be readily accessed and, as such conventional transmission radiographic techniques may be unavailable for non-destructive inspection purposes. Moreover, some structural components may be hidden by an overlying structure that has a thickness that is varied, thereby further complicating the radiographic inspection of the hidden structure since the results will also be dependent upon the thickness of the overlying structure through which the hidden structure was inspected. As such, many structural assemblies must be disassembled in order to inspect the structural components that are otherwise hidden from view, thereby materially increasing the time and the labor required for the inspection.

BRIEF SUMMARY

A method and system for non-destructively evaluating a workpiece hidden by an overlying structure are provided in accordance with an example embodiment of the present disclosure. In this regard, the method and system of one embodiment rely upon backscattered radiation such that access is only required to one side of the workpiece that is to be inspected. As such, a workpiece may be inspected in a non-destructive manner without disassembly or, at least, without significant disassembly, while requiring access to only one side of the workpiece. By relying upon backscattered radiation, such as backscattered x-rays, the method and system of one embodiment may detect and permit a workpiece that is hidden from view to be non-destructively inspected, thereby permitting evaluation and, if necessary, repair of the workpiece in an orderly manner.

In an example embodiment, a method is provided for non-destructively evaluating a workpiece hidden by an overlying structure. The method includes interrogating the workpiece with radiation, such as x-ray radiation, that also propagates through the overlying structure. The method further includes collecting data representative of radiation backscattered from the workpiece. Based upon a thickness and material of the overlying structure, the method compares the data that has been collected from the workpiece with reference data representative of radiation backscattered from a standard comprised of different respective material loss indicators hidden by an overlying structure of the same thickness and material. Each material loss indicator is a physical representation of a different amount of material loss. As a result of the comparison, the method estimates the material loss of the workpiece.

The method of an example embodiment may also include determining at least one of a maximum value, a minimum value or a delta value. The maximum value is the maximum value of the data representative of radiation backscattered from a portion of the workpiece. The minimum value is the minimum value of the data representative of radiation backscattered from the portion of the workpiece. The delta value represents a difference between the maximum and the minimum values of the data representative of radiation backscattered from the portion of the workpiece. In this example embodiment, the method compares the data that has been collected from the workpiece with reference data representative of radiation backscattered from different respective material loss indicators by comparing at least one of the maximum value, the minimum value or the delta value with corresponding values from the data representative of radiation backscattered from different respective material loss indicators hidden by an overlaying structure of the same thickness and material.

The comparison of the data that has been collected from the workpiece with reference data representative of radiation backscattered from different respective material loss indicators may, in one embodiment, be also based upon a material of the underlying structure such that the overlying structure that hides the workpiece during the interrogation of the workpiece is formed of the same material as the overlying structure that hides the standard during interrogation of the material loss indicators to acquire the reference data. The method of an example embodiment may also include receiving an indication of an area of interest of the workpiece and a number of sampling lines. The method of this example embodiment also includes identifying the data that has been collected along each respective sampling line. In this example embodiment, the method compares the data that has been collected from the workpiece with the reference data representative of radiation backscattered from different respective material loss indicators by separately comparing the data that has been collected along each respective sampling line with the reference data representative of radiation backscattered from different respective material loss indicators.

The method of an example embodiment compares the data that has been collected from the workpiece with the reference data representative of radiation backscattered from different respective material loss indicators hidden by an overlying structure of the same thickness and material by comparing gray scale levels representative of radiation backscattered from the workpiece with gray scale levels representative of radiation backscattered from the different respective material loss indicators. The method of an example embodiment interrogates the workpiece with radiation while the workpiece is hidden by the overall structure and without disassembly.

In another example embodiment, a system for non-destructively evaluating the workpiece hidden by an overlying structure is provided. The system includes a radiation source configured to interrogate the workpiece with radiation, such as x-ray radiation, that also propagates through the overlying structure. The system also includes a receiver configured to collect data representative of radiation backscattered from the workpiece. The system further includes a processor configured to compare, based upon the thickness and material of the overlying structure, the data that has been collected from the workpiece with reference data representative of radiation backscattered from a standard comprised of different respective material loss indicators hidden by an overlying structure of the same thickness and material. Each material loss indicator is a physical representation of a different amount of material loss. The processor is also configured to estimate, based upon the comparison, the material loss of the workpiece.

The processor of an example embodiment is also configured to determine at least one of a maximum value, a minimum value or a delta value. The maximum value is the maximum value of the data representative of radiation backscattered from a portion of the workpiece. The minimum value is the minimum value of the data representative of radiation backscattered from the portion of the workpiece. The delta value represents a difference between the maximum and minimum values of the data representative of radiation backscattered from the portion of the workpiece. The processor of this example embodiment is also configured to compare the data that has been collected from the workpiece with reference data representative of radiation backscattered from different respective material loss indicators by comparing at least one of the maximum value, the minimum value or the delta value with corresponding values from the data representative of radiation backscattered from different respective material loss indicators hidden by an overlying structure of the same thickness and material.

A comparison of the data that has been collected from the workpiece with reference data representative of radiation backscattered from different respective material loss indicators may also be based upon the material of the overlying structure such that the overlying structure that hides the workpiece during the interrogation of the workpiece is formed of the same material as the overlying structure that hides the standard during interrogation of the material loss indicators to acquire the reference data. The processor of an example embodiment is further configured to receive an indication of an area of interest of the workpiece and a number of sampling lines and to identify the data that has been collected along each respective sampling line. In this example embodiment, the processor is configured to compare the data that has been collected from the workpiece with the reference data representative of radiation backscattered from different respective material loss indicators by separately comparing the data that has been collected along each respective sampling line with the reference data representative of radiation backscattered from different respective material loss indicators.

The processor of an example embodiment is configured to compare the data that has been collected from the workpiece with the reference data representative of radiation backscattered from different respective material loss indicators hidden by an overlying material of the same thickness and material by comparing a gray scale level representative of radiation backscattered from the workpiece with gray scale levels representative of radiation backscattered from the different respective material loss indicators. The radiation source of an example embodiment is configured to interrogate the workpiece with radiation while the workpiece is hidden by the overlying structure without disassembly.

In a further example embodiment, a computing system for non-destructively evaluating a workpiece hidden by an overlying structure is provided. The computing system of this example embodiment includes a memory configured to store reference data representative of radiation backscattered from a standard comprised of different respective material loss indicators hidden by an overlying structure of the same thickness and material as that with which the workpiece is hidden. Each material loss indicator is a physical representation of a different amount of material loss. The computing system also includes a processor configured to compare, based upon the thickness and material of the overlying structure, data that has been collected and is representative of radiation backscattered from the workpiece with reference data stored by the memory that is representative of radiation backscattered from the standard comprised of different respective material loss indicators hidden by an overlying structure of the same thickness and material. The processor is also configured to estimate, based upon the comparison, a material loss of the workpiece.

The processor of an example embodiment is further configured to determine at least one of a maximum value, minimum value or a delta value. The maximum value is the maximum value of the data representative of radiation backscattered from a portion of the workpiece. The minimum value is the minimum value of the data representative of radiation backscattered from the portion of the workpiece. The delta value represents the difference between the maximum and minimum values of the data representative of radiation backscattered from the portion of the workpiece. The processor of this example embodiment is also configured to compare the data that has been collected from the workpiece with reference data representative of radiation backscattered from different respective material loss indicators by comparing at least one of the maximum value, the minimum value or the delta value with corresponding values from the data representative of radiation backscattered from different respective material loss indicators hidden by an overlying structure of the same thickness and material.

The comparison of the data that has been collected from the workpiece with reference data representative of radiation backscattered from different respective material loss indicators may also be based upon the material of the overlying structure such that the overlying structure that hides the workpiece during the interrogation of the workpiece is formed of the same material as the overlying structure that hides the standard during interrogation of the material loss indicators to acquire the reference data. The processor of an example embodiment is further configured to receive an indication of an area of interest of the workpiece and a number of sampling lines and to identify the data that has been collected along each respective sampling line. The processor of this example embodiment is also configured to compare the data that has been collected from the workpiece with the reference data representative of radiation backscattered from different respective material loss indicators by separately comparing the data that has been collected along each respective sampling line with the data representative of radiation backscattered from different respective material loss indicators.

The memory of an example embodiment is configured to store gray scale levels representative of radiation backscattered from the different respective material loss indicators. The processor of this example embodiment is configured to compare the data of that has been collected from the workpiece with the reference data representative of radiation backscattered from different respective material loss indicators hidden by an overlying structure of the same thickness and material by comparing gray scale levels representative of radiation backscattered from the workpiece with the gray scale levels representative of radiation backscattered from the different respective material loss indicators. The memory of an example embodiment is configured to store reference data representative of radiation backscattered from different respective material loss indicators hidden by overlying structures having different respective thicknesses.

BRIEF DESCRIPTION OF THE DRAWINGS

Figure 1:
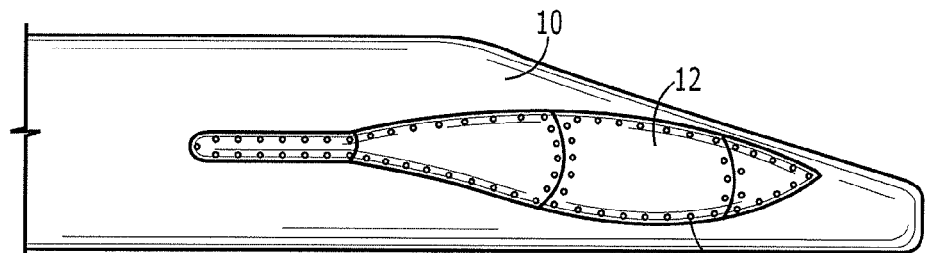
Figure 2:
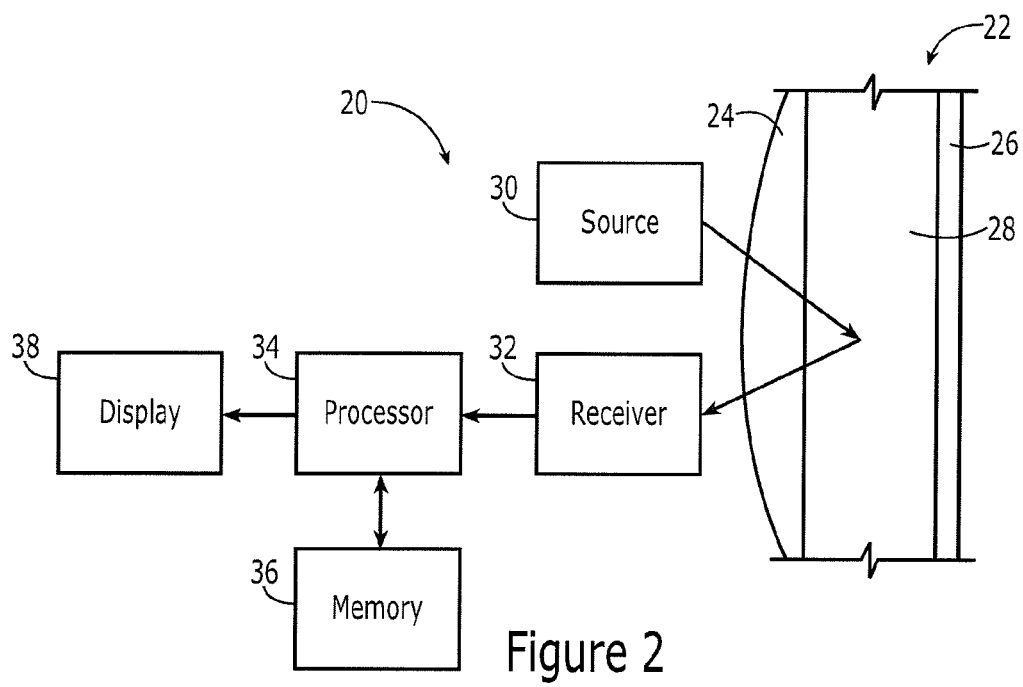
Figure 3:
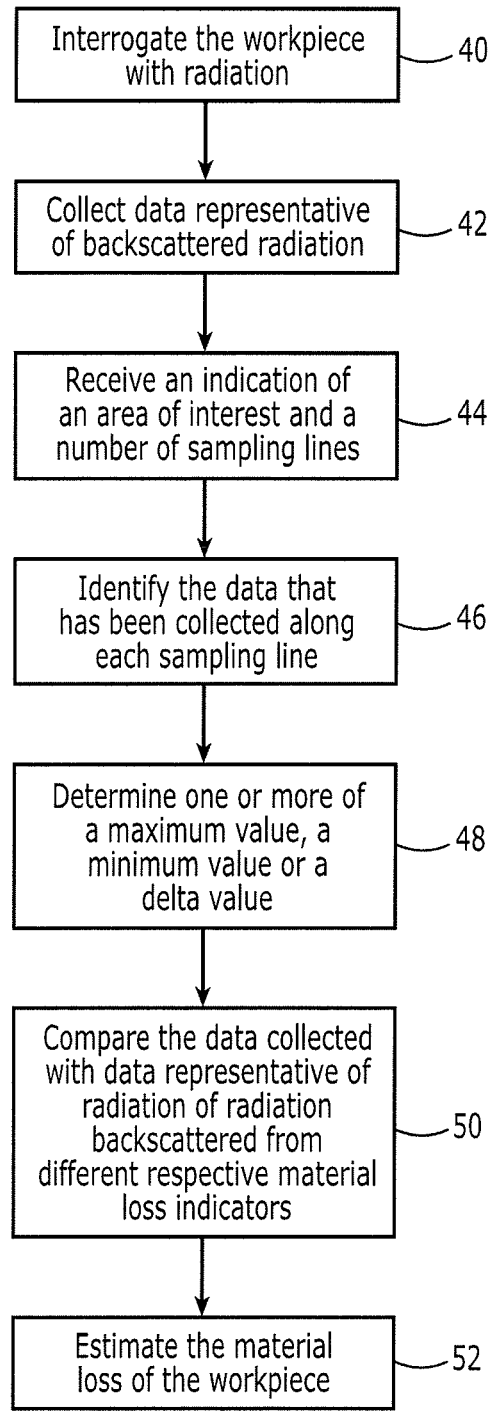
Figure 4:
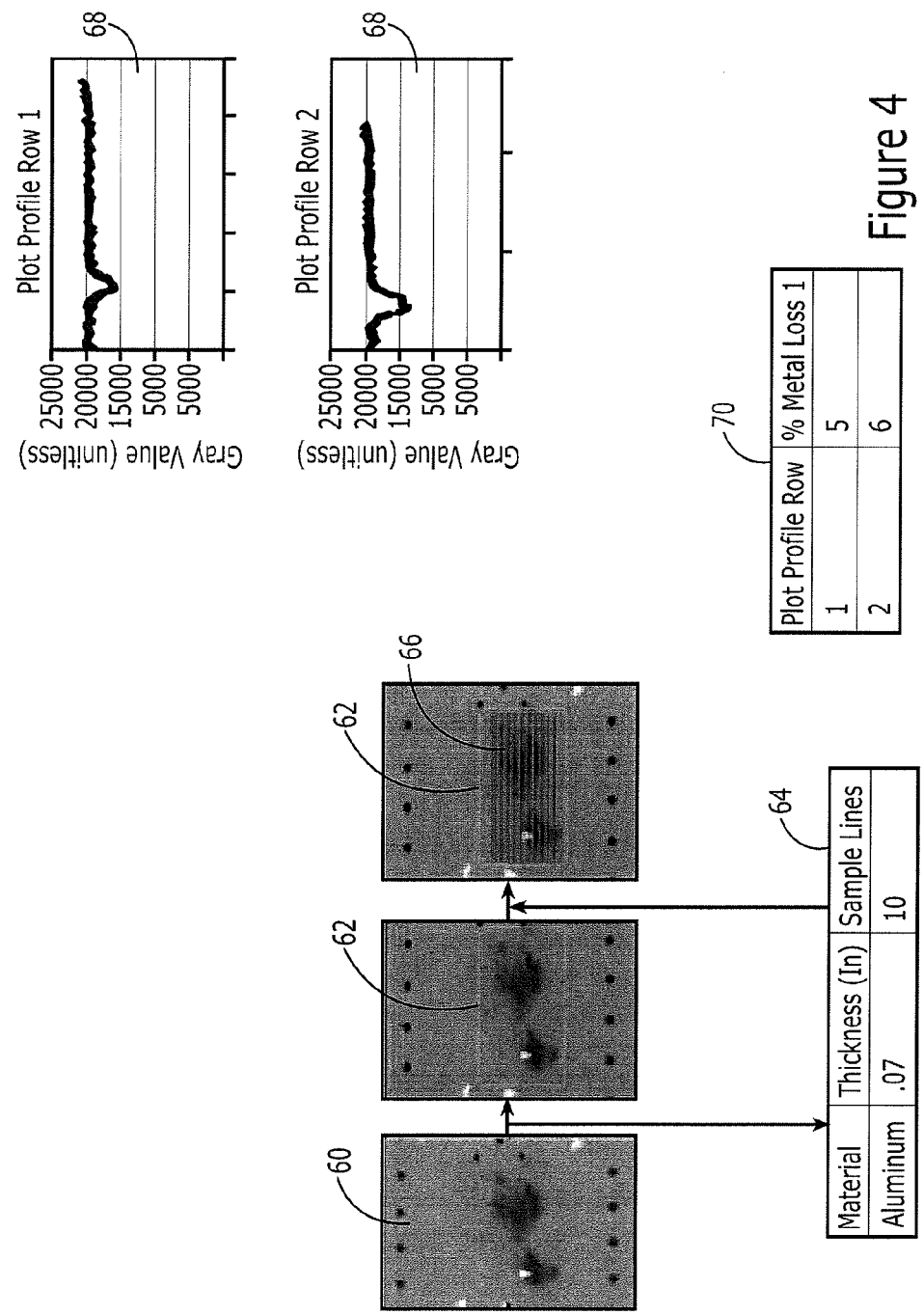
Figure 5:
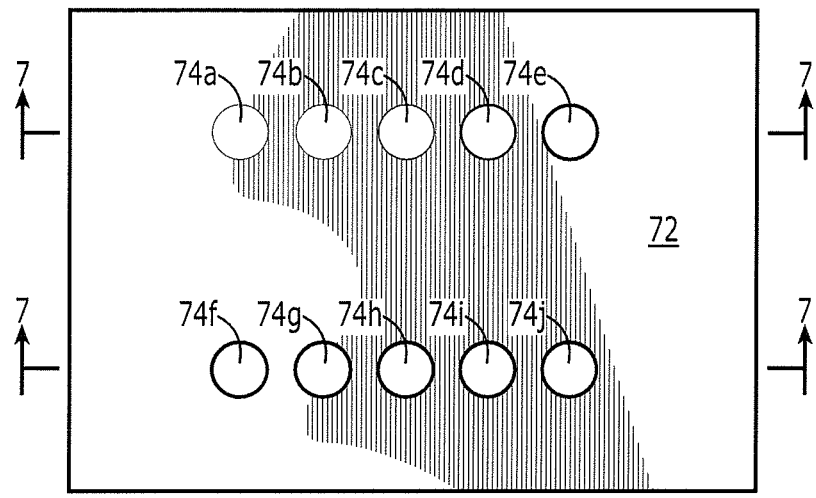
Figure 6:
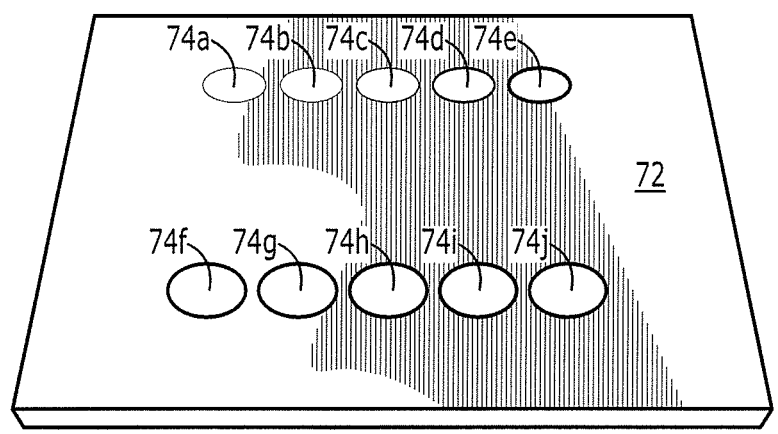
Figure 7A:
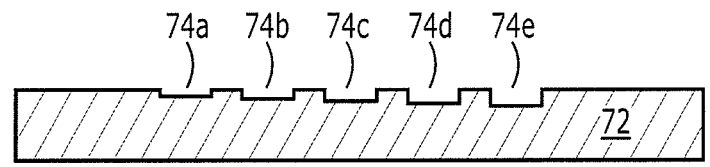
Figure 7B:
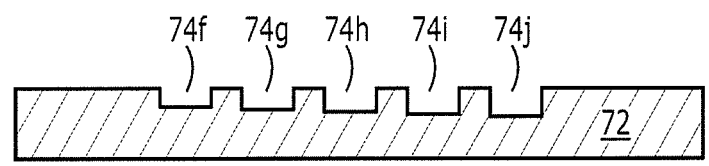
Figure 8:
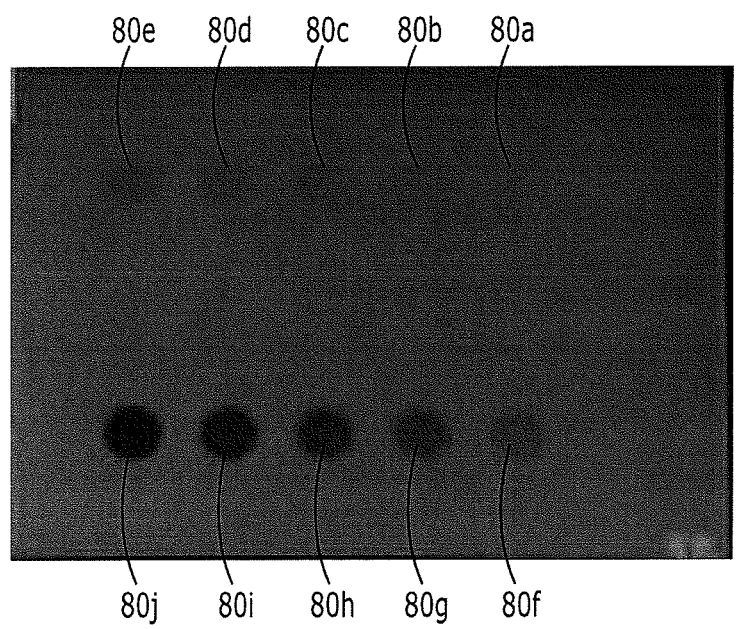
Figure 9:
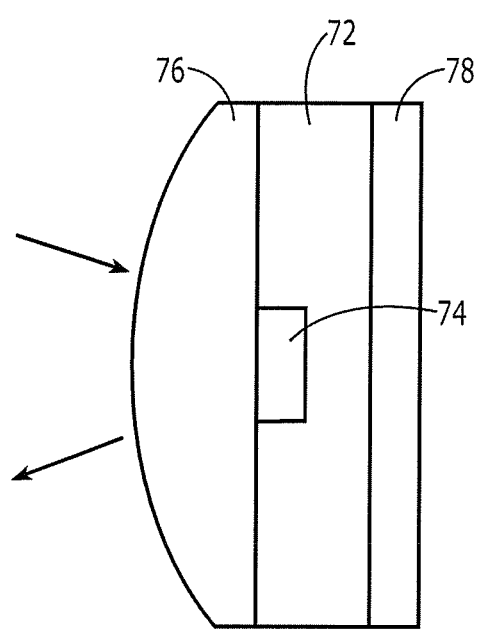

Having thus described example embodiments of the present disclosure in general terms, reference will now be made to the accompanying drawings, which are not necessarily drawn to scale, and wherein:

FIG. 1 depicts a portion of a wing having a beavertail fitting that may be inspected by the method and system of an example embodiment of the present disclosure;

FIG. 2 is a schematic representation of a system in accordance with one example embodiment of the present disclosure;

FIG. 3 is a flow chart of the operations performed in accordance with an example embodiment of the present disclosure;

FIG. 4 is a graphical representation of the operations performed to evaluate the data representative of the radiation backscattered from a workpiece in accordance with an example embodiment of the present disclosure;

FIG. 5 is a plan view of a plurality of material loss indicators in accordance with an example embodiment of the present disclosure;

FIG. 6 is a perspective view of the plurality of material loss indicators of FIG. 5;

FIGS. 7A and 7B are cross-sectional views of the plurality of material loss indicators taken along lines 7A-7A and 7B-7B, respectively, of FIG. 5;

FIG. 8 is the backscatter images of different material loss indicators that are generated in accordance with an example embodiment of the present disclosure; and FIG. 9 is a side view of the interrogation of a material loss indicator in accordance with an example embodiment of the present disclosure;.

DETAILED DESCRIPTION

The present disclosure now will be described more fully with reference to the accompanying drawings, in which some, but not all embodiments of the invention are shown. This disclosure may be embodied in many different forms and should not be construed as limited to the embodiments set forth; rather, these embodiments are provided so that this disclosure will be thorough and complete, and will fully convey the scope of the invention to those skilled in the art. Like numbers refer to like elements throughout.

A method and system are provided for non-destructively evaluating a workpiece hidden by an overlying structure. As used herein, a workpiece is hidden if all or a portion of the workpiece is hidden from view, that is, visually hidden, absent disassembly of a structural assembly including the workpiece. A variety of workpieces may be non-destructively evaluated. In this regard, the workpiece may be a structural component of a wide variety of different structural assemblies including, for example, vehicles, such as aircraft, trains, automobiles and other motor vehicles. However, the workpiece that is inspected may be a structural component of other types of structural assemblies, such as a building, a bridge or the like. Additionally, the workpiece may be formed of various materials, but in one embodiment, is formed of metal, such as aluminum.

While the method and system of an example embodiment may inspect workpieces that are visible or otherwise easily accessible and while the system and method of an example embodiment may inspect workpieces following disassembly of the structural assembly of which the workpiece is a structural component, the system and method of one embodiment is configured to inspect workpieces that are hidden in a manner that permits the workpiece to be interrogated or inspected without disassembly. In this regard, the workpiece may be hidden by an overlying structure, such as by being positioned within an interior portion of a structural assembly that has limited or remote access. For example, the workpiece that is inspected may be disposed within a structural assembly in a manner that the workpiece is hidden by an overlying structure and is unable to be viewed without disassembly of at least a portion of the structural assembly, such as by removal of the overlying structure. With respect to an aircraft, a number of structural components, such as stringers, are disposed within the aircraft in such a manner as not to be visible without disassembly of other portions of the aircraft.

By way of example, but not of limitation, FIG. 1 illustrates a portion of a wing 10 including a fitting 12, such as a beavertail fitting, attached to the wing skin by a plurality of fasteners 14. Like the wing skin, the fitting 12 may be formed of a metal, such as aluminum. The fitting may also have a profile and, therefore, a thickness that is varied with some portions of the fitting, such as medial portions, being thicker than other portions of the fitting, such as the peripheral or edge portions. Thus, a portion of the wing 10 is not visible without removal of the fitting 12 and, as such, is hidden from sight without disassembly. Since the removal of the fitting 12 would be time consuming due to the number of fasteners 14 utilized to secure the fitting to the wing 10, the hidden portion of the wing is advantageously inspected while the fitting remains in place. Moreover, the fitting 12, such as a beavertail fitting, may limit the utility of ultrasonic or eddy current inspection techniques such that a radiographic inspection technique may be utilized. In this regard, the plurality of fasteners 14 in combination with the thickness of the fitting 12 may limit the utility of ultrasonic or eddy current inspection techniques. Further, the curvature of the fitting 12 and the air gap between the fitting and the wing skin that would potentially suffer corrosion may further limit the utility of ultrasonic inspection techniques. With respect to radiographic inspection techniques, since access to both of the opposed sides of the wing skin is limited, the method and system of an example embodiment may utilize backscattered radiation in order to inspect the workpiece hidden by an overlying structure, such as the portion of the wing skin that underlies the fitting 12, such that access is only required to one side of the workpiece that is to be inspected. Further, the method and system of an example embodiment take into account the material thickness of the overlying structure, including variations in the thickness of the overlying structure, e.g., the curvature of the overlying structure, so as to improve the accuracy and reliability of the results of the inspection.

As shown in FIG. 2, a system 20 is provided for non-destructively evaluating a workpiece 28 of a structural assembly 22 that is hidden by an overlying structure 24. In the illustrated embodiment, the workpiece 28 not only is hidden by the overlying structure 24, but access to a rear surface of the workpiece may be limited, such as by another structure 26. The workpiece 28 of this embodiment is therefore sandwiched between and hidden from view by overlying structures 24, 26. Although hidden, the workpiece 28 may sometimes be subject to corrosion as a result of the intrusion and retention of moisture in a manner that is not visible without disassembly of the structural assembly 22. As such, the method and system of an example embodiment permit the effects of corrosion upon the workpiece 28, such as a workpiece hidden from sight, to be detected and visualized, thereby allowing decisions to be made with respect to any repairs and, if so, the timing of such repairs to be made in an orderly manner that does not disrupt or that at least limits the disruption in the schedule of the structural assembly 22.

The system 20 of FIG. 2 includes a source 30 of radiation. While various types of radiation may be employed, the source 30 of one embodiment is an x-ray source permitting x-rays to be generated. In this embodiment, the x-ray source 18 may have various power levels depending upon the thickness and radiation absorption characteristics of the workpiece 28 and the thickness and radiation absorption characteristics of the other structural components surrounding the workpiece. In one embodiment, however, the x-ray source 30 is a 160 kv x-ray tube, while in another embodiment, the x-ray source is a 220 kv x-ray tube. Indeed, depending upon the workpiece 28 to be inspected and the structural assembly 22 of which the workpiece is a component, the exposure requirements, such as the kilovoltage, milliamperage, scan speed and stand-off distance, may be modified.

As shown in block 40 of FIG. 3, the source 30 is configured to interrogate the workpiece 28 with radiation, such as by interrogating the workpiece with x-ray radiation. While the workpiece 28 may be interrogated in various manners, the source 30 of one embodiment is configured to generate a relatively small beam of radiation, such as a pencil-sized beam of radiation, that is scanned, such as by being raster scanned, across the workpiece or at least a portion of the workpiece. The beam of radiation may be scanned in various manners, but, in one embodiment, the source 30 includes a rotating collimator that directs one or more beams of radiation across the workpiece 28 in a predefined pattern, such as by directing one or more beams of radiation along predefined lines across the workpiece.

The impingement of the radiation, such as the x-rays, upon the workpiece 28 causes photons to be backscattered. As such, the system 20 of FIG. 2 includes a receiver 32, such as a photon detector, for capturing the photons scattered by the workpiece 28 as a result of the impingement of the radiation thereon. Based upon the radiation backscattered from the workpiece 28, such as the scattered photons captured by the receiver 32, such as the photon detector, the system 20 collects data representative of the radiation backscattered from the workpiece, as shown in block 42 of FIG. 3. The scattered photons generated by the impingement of the radiation upon the workpiece 28 that are detected by the receiver 32, such as a photon detector, may, in one embodiment, be processed, such as by a processor 34, so as to generate a backscatter image of the workpiece based upon radiation backscattered from the workpiece. The backscatter image that is generated may be presented upon a display 38 that is driven by the receiver 32 and, in turn, by the processor 34. Additionally or alternatively, the data collected by the receiver 32 that is representative of the radiation backscattered from the workpiece 28 may be stored by the memory 36.

Although various types of backscatter images may be generated, one example of a backscatter image is shown at 60 in FIG. 4. While the backscatter images may be presented in color, the backscatter images of one embodiment are black and white images with the effects of corrosion generally indicated by a darker region of the image that is representative of thinner portions of the workpiece 28, such as portions of the workpiece that have been thinned as a result of the loss of material due to corrosive effects. In this regard, the example image 60 of FIG. 4 includes two regions that may have been subjected to corrosion as a result of the two darker areas within the image.

By relying upon backscattered photons in order to generate the image of the workpiece 28, both the source 30 of the radiation and the receiver 32, processor 34 and display 38 may be positioned upon the same side of the workpiece. As such, the method and system of this embodiment not only permits a workpiece 28 to be interrogated in an instance in which the workpiece is hidden and without requiring disassembly of the structural assembly 22 that includes the workpiece, but permits the non-destructive inspection to be performed from a single side of the workpiece, thereby avoiding any need for access to the opposite sides of the workpiece. As a result, the method and system 20 of an example embodiment are able to inspect a greater number of workpieces 28 since the method and system of an example embodiment are able to inspect workpieces that cannot be accessed from both sides.

As shown in block 44 of FIG. 3, the processor 34 of an example embodiment is configured to receive an indication of an area of interest from within the backscatter image of the workpiece 28. As the area of interest identifies the portion of the backscatter image of the workpiece 28 that will be evaluated in more detail, the area of interest is generally defined so as to include those regions that appear, at least initially, to have been subject to corrosion, such as evidenced by the darker areas of the backscatter image. With respect to the backscatter image 60 of FIG. 4, the area of interest 62 may be defined so as to include the two darker regions that may have been subject to corrosion. The area of interest 62 may be defined in various manners including the receipt of coordinates from a technician defining the bounds of the area of interest, by the sizing of a graphical representation of the area of interest upon the backscatter image, by user interaction with the backscatter image via touch screen or the like. In addition, the processor 34 is configured to receive, such as in the form of user input, an indication of the number of sampling lines along with the data that has been collected and that is representative of the backscattered radiation will be analyzed in greater detail, as described below. In the example depicted in FIG. 4, the technician indicates that the data within the area of interest should be evaluated along ten sampling lines. In response, the processor 34 of an example embodiment defines a number of sampling lines that extend across the area of interest 62 parallel to one another and with equal spacing. As shown in FIG. 4, the processor 34 may also be configured to receive, such as via entry by a technician, indications of the material of the overlying structure 24 and the thickness of that portion of the overlying structure that overlies the area of interest 62 of the workpiece 28. Although the overlying structure may have a constant thickness, the overlying structure of an example embodiment has a curved profile and, as such, has a thickness that is different depending upon the relative location of the area of interest 62.

As shown in block 46 of FIG. 3, the processor 34 is also configured to identify the data that has been collected along each sampling line. As shown by the plot profiles 68 of FIG. 4, the processor 34 of an example embodiment is configured to graphically represent the data that has been collected along each sampling line with the resulting plots being displayed, in some embodiments, upon the display 38. FIG. 4 depicts the plot profiles 68 for sampling lines 1 and 2 with the processor 34 of this example embodiment also being configured to generate the plot profiles for the other sampling lines in a comparable manner. The plot profiles 68 graphically represent the gray scale value of each pixel (associated with a respective element of the receiver 32) along the sampling line, such as from left to right, right to left or the like. A decrease in the gray scale value may be indicative of a region of the workpiece 28 that has experienced a loss of material, such as due to corrosion, and is therefore evaluated in more detail as described below.

The processor 34 of an example embodiment is configured to determine various parameters associated with the data that has been collected along each sampling line. See block 48 of FIG. 3. For example, the processor 34 of an example embodiment is configured to determine the maximum value of the data representative of radiation backscattered from a portion of the workpiece 28 along a respective sampling line. The processor of this example embodiment then determines those portions of the data that has been collected along the respective sampling line that is indicative of a potential loss of material. In this regard, the processor may identify those portions of the data having a value that deviate from, such as by being less than, the maximum value by at least a predetermined threshold amount. With respect to the plot profile 68 of the data that has been collected along each of the sampling lines and is depicted in FIG. 4, the processor 34 is configured to determine each instance along a sampling line for which the data falls below the maximum value by at least the predetermined threshold amount, thereby identifying each valley, one of which is shown in each plot profile. For each segment, e.g., valley, along the sampling line that deviates from the maximum value by at least a predetermined amount, the processor 34 is configured to determine the minimum value of the data representative of radiation backscattered from the respective segment of the workpiece 28.

Additionally, the processor 34 of an example embodiment is configured to determine a delta value representing a difference between the maximum and minimum values of the data representative of radiation backscattered from the workpiece 28. The delta value may be expressed in various manners including in terms of the difference in gray scale values between the maximum and minimum values or a percentage decrease in gray scale values from the maximum values to the minimum value.

As shown in block 50 of FIG. 3, the processor 34 is configured to compare the data that has been collected from the workpiece to the reference data that has been previously collected and is representative of radiation backscattered from a standard comprised of different respective material loss indicators 74. In this regard, each material loss indicator 74 is a physical representation of a different amount of material loss with the material loss indicator having been interrogated with radiation while being hidden by an overlying structure of the same thickness and of the same material that overlies the area of interest 62 of the workpiece 28. While the data that has been collected may be compared in various manners with the reference data representative of the radiation backscattered from a standard comprised of different respective material loss indicators hidden by an overlying structure of the same thickness, at least one of the maximum value, the minimum value or the delta value of the data that has been collected and that is representative of radiation backscattered from the workpiece 28 may be compared to corresponding values derived from the reference data representative of radiation backscattered from a standard comprised of different respective material loss indicators hidden by an overlying structure of the same thickness and material. For example, the delta value, such as the percentage difference between the minimum value and maximum value of the data that has been collected and is representative of radiation backscattered from the workpiece 28, may be compared with a corresponding delta value derived from the reference data representative of radiation backscattered from each of the different respective material loss indicators 74 that were interrogated while hidden by an overlying structure of the same thickness and the same material.

As referenced herein, the comparison also includes a determination as to the interrogation of which, if any, of the different material loss indicators 74 generate data have a parameter value, e.g., a delta value, that matches the corresponding value derived from the data representative of the radiation backscattered by the workpiece 28. The comparison may determine an instance in which the values match, such as in an instance in which the value, e.g., the delta value, derived from the data representative of radiation backscattered from the workpiece 28 matches the corresponding value derived from the data representative of radiation backscattered from a respective material loss indicator 74. In this regard, corresponding values may be considered to match one another in an instance in which the corresponding values are identical or are within a predefined range of one another. This comparison may be performed manually, such as by an inspector or other technician, or in an automated manner, such as by the processor 34.

Each material loss indicator 74 may be representative of a different amount, such as a different percentage, of material loss and, as such, serves as a standard. Although material loss indicators 74 may be discrete and individualized indicators, a plurality of material loss indicators of one example are shown in FIGS. 5 and 6. In this regard, a material loss indicator panel 72 includes a plurality of material loss indicators 74. The material loss indicator panel 72 has a predefined thickness, such as 0.375 inches in one example embodiment, and is formed of a material, such as a metal, e.g., aluminum, that may be interrogated by radiation, e.g., x-rays. In one embodiment, the material loss indicator panel 72 is formed of a material having the same radiation absorption characteristics as the workpiece 28, such as by being formed of the same material as the workpiece. The material loss indicator panel 72 may also have the same thickness as the workpiece 28, but may have a different thickness than the workpiece in other embodiments. Each material loss indicator 74 of the material loss indicator panel 72 is a region of the material loss indicator panel from which a different thickness of material has been removed. In one embodiment, for example, each material loss indicator 74 may be representative of a different percentage of material loss. See FIGS. 7A and 7B. Indeed, in one embodiment, the plurality of material loss indicators 74 representative of respective percentages of material loss are more closely spaced for smaller percentages than for larger percentages in order to facilitate the resolution with which material loss attributable to corrosion may be detected by the system and method of an example embodiment. Although the material loss indicators 74 may be representative of different amounts, such as different percentages, of material loss, the material loss indicators 74a, 74b, 74c, 74d, 74e, 74f, 74g, 74h, 74i and 74j of one embodiment may be representative of the removal of one percent, two percent, three percent, four percent, five percent, ten percent, fifteen percent, twenty percent, and thirty percent, respectively, of the thickness of the material loss indicator panel 72. In one embodiment, the material loss indicator panel 72 has a different thickness than the workpiece 28, but the material loss indicators advantageously represent different percentages of material loss relative to the thickness of the workpiece.

In the illustrated embodiment, the plurality of material loss indicators 74 are formed by removing material from a material loss indicator panel 72 that is otherwise of a uniform thickness. However, the material loss indicators 74 need not be formed by the removal of material, but, instead, the material loss indicators may be initially formed so as to define regions that are thinner than other regions of the material loss indicator panel 72. Additionally, while a material loss indicator panel 72 including a plurality of material loss indicators 74 is shown in FIGS. 5 and 6 and will be described herein by way of example, the plurality of material loss indicators need not be carried by a single material loss indicator panel, but may instead be separated from one another.

The backscatter images of the material loss indicators 74 may be generated by irradiating the material loss indicators, such as with x-rays. In one embodiment, either the same or a different source 30 of radiation may irradiate the material loss indicators 74, such as by scanning a beam of radiation across the material loss indicators and then capturing the photons that are scattered, such as with a receiver 32, e.g., a photon detector. Based upon the captured photons, data representative of the radiation backscattered from the different material loss indicators 74 may be collected and, in one embodiment, backscatter images of the material loss indicators may be generated, such as by the processor 34, and displayed, such as upon a display. See, for example, FIG. 8. The data representative of the radiation backscattered from the different material loss indicators 74 that is collected may also be stored by memory 36 so as to be available for subsequent review.

During the interrogation of the material loss indicators 74, the material loss indicator panel 72 may be hidden, as shown in FIG. 9, by an overlying structure 76 in the same manner that the workpiece 28 that is being inspected is being hidden by an overlying structure 24. In this regard, the overlying structure 76 that hides the material loss indicator panel 72 may be formed of the same material and may have the same thickness as the overlying structure 24 that hides the workpiece 28 that is undergoing inspection, separate from the interrogation of the material loss indicators 74. In some embodiments, the material loss indicators 74 may be separately interrogated and data representative of the backscattered radiation may be collected while the material loss indicator panel 72 is hidden by overlying structures 76 of different thickness so as to provide a richer data set that may, in turn, be stored by memory 36. Optionally, the material loss indicator panel 72 may also be backed by a structural panel 78 that is similar to the structural component(s) that back the workpiece 28 undergoing inspection. In this regard, the structural panel 78 that backs the material loss indicator panel 72 may be formed of the same material and may have the same thickness as the structural component(s) that back the workpiece 28 undergoing inspection. As such, the data representative of the radiation backscattered from the different material loss indicators 74 of the material loss indicator panel 72 may be more accurately compared to the data that is representative of radiation backscattered from the workpiece 28 undergoing inspection since the overlying structure that hides the workpiece during the interrogation of the workpiece is formed of the same material and has the same thickness as the overlying structure that hides the material loss indicators during interrogation of the material loss indicators.

As indicated above, the data collected during interrogation of the workpiece 28 and the material loss indicator panel 72 may be representative of a backscatter image of the workpiece 28 and backscatter images of different material loss indicators 74. The backscatter images of different material loss indicators 74 of one embodiment, such as the backscatter images of the material loss indicators of the material loss indicator panel 72 of FIGS. 5 and 6, are shown in FIG. 8. The backscatter images of the material loss indicators 74 may be presented in various manners including with various colors, but, in one embodiment, are presented in black and white with various gray scale levels being indicative of the thickness of the material. In this regard, thinner regions of material may be indicated by darker regions of the image with the darkness of the image varying directly, such as proportionately, with the thinness of the materials. As such, in this embodiment, those regions of the material being inspected that are thinner create darker regions of the backscatter image, while those regions of the material being inspected that are thicker create lighter regions of the backscatter image.

The backscatter images of the different material loss indicators 74 that are shown in FIG. 8 include backscatter images 80a, 80b, 80c, 80d, 80e, 80f, 80g, 80h, 80i and 80j that correspond to the backscatter images generated by interrogation of material loss indicators 74a, 74b, 74c, 74d, 74e, 74f, 74g, 74h, 74i and 74j, respectively. As will be apparent, the gray scale levels of the backscatter images associated with the different material loss indicators 74 become progressively darker as the images progress from the image generated by the material loss indicator representative of the thickest sample from which the least material has been lost, that is, material loss indicator 74a and corresponding backscatter image 80a, to the backscatter image of the material loss indicator that is representative of the thinnest sample from which the most material has been lost, that is, material loss indicator 74j and corresponding backscatter image 80j.

As shown in block 52 of FIG. 3, the processor 34 is also configured to estimate the material loss experienced by the workpiece 28. Based upon the comparison of the data that has been collected to the data representative of radiation backscattered from different respective material loss indicators 74, the processor 34 is configured to determine the interrogation of which, if any, of the different material loss indicators 74 generates data having a parameter value, e.g., a delta value, that matches the corresponding value derived from the data representative of the radiation backscattered by the workpiece 28. The predefined material loss, such as the predefined percentage of material loss, that is associated with the material loss indicator that is determined to be a match then serves as the estimate of the material loss experienced by the workpiece 28. For example, in an instance in which the processor 34 determines that the interrogation of the material loss indicator 74 associated with a 10% loss of material generates data having a parameter value, e.g., a delta value, that matches the corresponding value derived from the data representative of the radiation backscattered by the workpiece 28, the processor estimates the material loss of the workpiece to also be 10%.

Once the material loss attributable to corrosion is identified and, in some instances, estimated, a determination may be made as to whether the workpiece 28 requires repair and, if so, if the repair should be performed immediately or at some later time. If a repair may be made at a later time, the repair may be scheduled at a more convenient time, such as in an instance in which the structural assembly of which the workpiece 28 is a component is otherwise going to be subjected to inspection and repair. For example, in an instance in which the workpiece 28 is a structural component of an aircraft, the repair may be scheduled for the next time that the aircraft is going to visit the repair depot for routine maintenance, thereby avoiding the adverse impacts of having to take the aircraft out of service unexpectedly.

Many modifications and other embodiments set forth herein will come to mind to one skilled in the art to which these embodiments pertain having the benefit of the teachings presented in the foregoing descriptions and the associated drawings. Therefore, it is to be understood that the embodiments are not to be limited to the specific ones disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions other than those explicitly described above are also contemplated as may be set forth in some of the appended claims. Although specific terms are employed herein, they are used in a generic and descriptive sense only and not for purposes of limitation.

That which is claimed:

1. A method for non-destructively evaluating a workpiece hidden by a first overlying structure, the method comprising:
   interrogating the workpiece hidden by the first overlying workpiece with x-ray radiation that propagates through the first overlying structure;
   collecting data representative of x-ray radiation backscattered from the workpiece, wherein collecting data comprises collecting data representative of x-ray radiation backscattered from the workpiece along a plurality of sampling lines;
   receiving an indication of an area of the workpiece;
   identifying the data that has been collected along the plurality of sampling lines that extend across the area of the workpiece;
   for each sampling line, determining at least one of a maximum value of the data representative of x-ray radiation backscattered from the workpiece, a minimum value of the data representative of x-ray radiation backscattered from the workpiece or a delta value representing a difference between the maximum and minimum values of the data representative of x-ray radiation backscattered from the workpiece;
   based upon a thickness and material of the first overlying structure, comparing, with a processor, the data that has been collected from the workpiece with reference data representative of x-ray radiation backscattered from a standard comprised of different respective material loss indicators hidden by a reference overlying structure of the same thickness and material as the first overlying structure, each material loss indicator being a physical representation of a different known amount of material loss, wherein comparing the data that has been collected from the workpiece with the reference data representative of x-ray radiation backscattered from the standard comprised of different respective material loss indicators comprises separately comparing, for each respective sampling line, at least one of the maximum value, the minimum value or the delta value that has been collected along and determined for each respective sampling line with with a corresponding maximum value of the data representative of the x-ray radiation backscattered from the standard, a corresponding minimum value of the data representative of the x-ray radiation backscattered from the standard or a corresponding delta value representing a difference between the corresponding maximum and the corresponding minimum values of the data representative of x-ray radiation backscattered from the standard; and as a result of the comparing, calculating, with the processor, an estimated amount of a material loss of the workpiece.

2. A method according to claim 1 further comprising: receiving a number of sampling lines.

3. A method according to claim 1, wherein comparing the data that has been collected from the workpiece with the reference data representative of x-ray radiation backscattered from the standard comprised of different respective material loss indicators hidden by the reference overlying structure of the same thickness and material as the first overlying structure comprises comparing grey scale levels representative of x-ray radiation backscattered from the workpiece with grey scale levels representative of x-ray radiation backscattered from the standard comprised of the different respective material loss indicators.

4. A method according to claim 1, wherein interrogating the workpiece with x-ray radiation comprises interrogating the workpiece while hidden by the first overlying structure and without disassembly.

5. A system for non-destructively evaluating a workpiece hidden by a first overlying structure, the system comprising:
a radiation source configured to interrogate the workpiece hidden by the first overlying workpiece with x-ray radiation that propagates through the first overlying structure;
a receiver configured to collect data representative of x-ray radiation backscattered from the workpiece, wherein the receiver is configured to collect data representative of x-ray radiation backscattered from the workpiece along a plurality of sampling lines; and
a processor configured to receive an indication of an area of the workpiece, identify the data that has been collected along the plurality of sampling lines that extend across the area of the workpiece, determine, for each sampling line, at least one of a maximum value of the data representative of x-ray radiation backscattered from the workpiece, a minimum value of the data representative of x-ray radiation backscattered from the workpiece or a delta value representing a difference between the maximum and minimum values of the data representative of x-ray radiation backscattered from the workpiece and compare, based upon a thickness and material of the first overlying structure, the data that has been collected from the workpiece with reference data representative of x-ray radiation backscattered from a standard comprised of different respective material loss indicators hidden by a reference overlying structure of the same thickness and material as the first overlying structure, each material loss indicator being a physical representation of a different known amount of material loss, wherein the processor is configured to compare the data that has been collected from the workpiece with the reference data representative of x-ray radiation backscattered from the standard comprised of different respective material loss indicators by separately comparing, for each respective sampling line, at least one of the maximum value, the minimum value or the delta value that has been collected along and determined for each respective sampling line with a corresponding maximum value of the data representative of the x-ray radiation backscattered from the standard, a corresponding minimum value of the data representative of the x-ray radiation backscattered from the standard or a corresponding delta value representing a difference between the corresponding maximum and the corresponding minimum values of the data representative of x-ray radiation backscattered from the standard, and wherein the processor is also configured to calculate, based upon the comparing, an estimated amount of a material loss of the workpiece.

6. A system according to claim 5 wherein the processor is further configured to receive a number of sampling lines.

7. A system according to claim 5, wherein the processor is configured to compare the data that has been collected from the workpiece with the reference data representative of x-ray radiation backscattered from the standard comprised of different respective material loss indicators hidden by the reference overlying structure of the same thickness and material as the first overlying structure by comparing grey scale levels representative of x-ray radiation backscattered from the workpiece with grey scale levels representative of x-ray radiation backscattered from the standard comprised of the different respective material loss indicators.

8. A system according to claim 5, wherein the radiation source is configured to interrogate the workpiece with x-ray radiation while the workpiece is hidden by the first overlying structure and without disassembly.

9. A computing system for non-destructively evaluating a workpiece hidden by a first overlying structure, the computing system comprising:
a memory configured to store reference data representative of x-ray radiation backscattered from a standard comprised of different respective material loss indicators hidden by a reference overlying structure of a same thickness and material as the first overlying structure with which the workpiece is hidden, each material loss indicator being a physical representation of a different known amount of material loss; and
a processor configured to receive an indication of an area of the workpiece, identify the data that has been collected along a plurality of sampling lines that extend across the area of the workpiece, determine, for each sampling line, at least one of a maximum value of the data representative of x-ray radiation backscattered from the workpiece, a minimum value of the data representative of x-ray radiation backscattered from the workpiece or a delta value representing a difference between the maximum and minimum values of the data representative of x-ray radiation backscattered from the workpiece and compare, based upon the thickness and material of the first overlying structure, data that has been collected and is representative of x-ray radiation backscattered from the workpiece with the reference data stored by the memory that is representative of x-ray radiation backscattered from the standard comprised of different respective material loss indicators hidden by the reference overlying structure of the same thickness and material as the first overlying structure, wherein the processor is configured to compare the data that has been collected from the workpiece with the reference data representative of x-ray radiation backscattered from different respective material loss indicators by separately comparing, for each respective sampling line, at least one of the maximum value, the minimum value or the delta value that has been collected along and determined for each respective sampling line with a corresponding maximum value of the data representative of the x-ray radiation backscattered from the standard, a corresponding minimum value of the data representative of the x-ray radiation backscattered from the standard or a corresponding delta value representing a difference between the corresponding maximum and the corresponding minimum values of the data representative of x-ray radiation backscattered from the standard, and wherein the processor is also configured to calculate, based upon the comparing, an estimated amount of a material loss of the workpiece.

10. A computing system according to claim 9 wherein the processor is further configured to receive a number of sampling lines.

11. A computing system according to claim 9, wherein the memory is configured to store grey scale levels representative of x-ray radiation backscattered from the standard comprised of the different respective material loss indicators, and wherein the processor is configured to compare the data that has been collected from the workpiece with the reference data representative of x-ray radiation backscattered from the standard comprised of different respective material loss indicators hidden by the reference overlying structure of the same thickness and material as the first overlying structure by comparing grey scale levels representative of x-ray radiation backscattered from the workpiece with the grey scale levels representative of x-ray radiation backscattered from the standard comprised of the different respective material loss indicators.

12. A computing system according to claim 9, wherein the memory is configured to store reference data representative of x-ray radiation backscattered from different respective material loss indicators hidden by overlying structures having different respective thicknesses.

* * * * *